United States Patent
Ishikawa et al.

[11] Patent Number: 6,024,450
[45] Date of Patent: Feb. 15, 2000

[54] DISEASE JUDGING APPARATUS

[75] Inventors: Norio Ishikawa; Katsumi Nakaichi; Hidehiro Hosaka, all of Tokyo; Munetaka Haida, Kanagawa; Yukito Shinohara, Tokyo, all of Japan

[73] Assignee: Nihon Kohden Corporation, Tokyo, Japan

[21] Appl. No.: 08/895,275

[22] Filed: Jul. 16, 1997

[30] Foreign Application Priority Data

Jul. 16, 1996 [JP] Japan ................................ 8-185973

[51] Int. Cl.[7] ........................................... A61B 3/10
[52] U.S. Cl. ................................. 351/221; 351/205
[58] Field of Search .................................. 351/221, 205, 351/206, 209, 200, 246, 247

[56] References Cited

U.S. PATENT DOCUMENTS 5,704,369  1/1998  Scinto et al. ............................ 728/745

FOREIGN PATENT DOCUMENTS 0 743 040 A1  11/1996  European Pat. Off. .......... A61B 3/11
WO 96/03070   2/1996   WIPO .......................... A61B 3/11

OTHER PUBLICATIONS

"Science" (vol. 266, Nov. 11, 1994) pp. 1051–1054.

*Primary Examiner*—Hung X. Dang
*Attorney, Agent, or Firm*—Sughrue, Mion, Zinn Macpeak & Seas, PLLC

[57] ABSTRACT

A pupil dilating dilution is dropped into one of the left eye or the right eye of a subject. Video cameras 1A, 1B are directed toward the bulbs of the eyes 22A, 22B, and output video signals on the pupils of both left and right eyes. These video signals are delivered to an area calculating circuit 7 through video camera control units 4A, 4B and an image receiving circuit 6. The area calculating circuit 7 calculates the areas of the given pupils of both left and right eyes, and applies the calculated results to a digital computer 8. The digital computer 8 calculates a difference between the given pupil areas of both the left and right eyes, calculates an index value relating to the magnification of the pupil area based on the calculated difference, and judges whether or not the subject is affected with Alzheimer's disease.

8 Claims, 9 Drawing Sheets

FIG. 9

DISEASE JUDGING APPARATUS

BACKGROUND OF THE INVENTION

1. Field of the Invention

The invention relates to an improvement of a disease judging apparatus that examines and diagnoses Alzheimer's disease and the like by measuring areas of the pupils of a subject.

2. Related Art

It has recently been revealed that whether or not a subject is affected with Alzheimer's disease can be diagnosed by dropping a pupil dilating dilution into an eye of the subject, measuring the diameter (area) of the pupil of the eye, and calculating the magnification after dropping the pupil dilating dilution (a U.S. periodical "SCIENCE" (VOL. 266, Nov. 11, 1994)). A method therefor involves the steps of: dropping a pupil dilating dilution into, e.g., the left eye of a subject and a physiological saline to the right eye; measuring the magnification of the pupil area for a time period lasting for 30 to 60 minutes thereafter; and judging whether or not the subject has contracted Alzheimer's disease from the calculated magnification.

Further, eyedrop tests in which a special eyedrops is applied to a subject in order to check that the subject suffers from autonomic unbalance have heretofore been conducted. In these eyedrops tests, a pupil is photographed before and after the eyedrops have been dropped, and the size of the pupil of the left eye and that of the right eye are measured using a ruler and compared with one another.

For example, an apparatus according to the prior art which is based on a pupil dilating dilution dropping method measures the area of the pupil of the right eye into which the physiological saline has been dropped, but such measured value is used only for reference. That is, when the apparatus according to the prior art judges whether or not a subject has contracted Alzheimer's disease, it is only the magnification of the left eye into which the pupil dilating dilution has been dropped that is used as an index value. Further, in order to judge whether or not a subject suffers from autonomic unbalance, it is only the magnification of the pupil of the left eye into which a special eyedrops (1.25% epinephrine, 5% tyramine, 5% cocaine, etc.) has been dropped that is measured.

A pupil expands widely in a dark place and contracts in a well-lighted place. Further, a pupil dilates and contracts due to influences derived from an autonomic nerve phyletic line. For example, when a person is surprised, his or her pupils dilate widely. Therefore, the magnification of the pupil area measured by the apparatus according to the prior art is such influenced data, and is, hence, not considered a genuine magnification that is derived only from the dropping of the eyedrops. As a result, it has been difficult to make a correct judgment on whether or not a subject suffers from Alzheimer's disease or autonomic unbalance.

SUMMARY OF THE INVENTION

The invention has been made to overcome these problems. The object of the invention is, therefore, to correctly measure a change in the size of a pupil, the change being dependent only on the dropping of eyedrops, and to correctly judge whether or not a subject suffers from Alzheimer's disease or autonomic unbalance.

A first aspect of the invention is applied to a disease judging apparatus that includes: a video camera device for imaging pupils of a left eye and a right eye of a subject with either the left eye or the right eye having eyedrops dropped thereinto; pupil size detecting means for calculating a size of the pupil of the left eye and a size of the pupil of the right eye for a plurality of times by processing video output signals from the video camera device; index value detecting means for calculating an index value relating to a change in the size of the pupil into which the eyedrops have been dropped from the sizes of the pupils of the left eye and the right eye detected at the respective times by the pupil size detecting means; and judging means for judging whether or not the subject suffers from a specific disease by comparing the index value calculated by the index value detecting means with a set value.

A second aspect of the invention is applied to a disease judging apparatus according to the first aspect of the invention, which is characterized in that the index value detecting means calculates the index value based on a difference between a rate of time-dependent change in the size of the pupil of the left eye and a rate of time-dependent change in the size of the pupil of the right eye.

A third aspect of the invention is applied to a disease judging apparatus according to the first aspect of the invention, which is characterized in that the index value detecting means calculates the index value based on a rate of time-dependent change in a difference between a size of the pupil of the left eye and a size of the pupil of the right eye.

BRIEF DESCRIPTION OF THE DRAWINGS

FIG. 4(*a*)–FIG. 4(*b*) are timing charts illustrative of the operation of a receiving circuit;

DETAILED DESCRIPTION OF THE PREFERRED EMBODIMENT

A first embodiment of the invention will now be described. The principle of this embodiment will be described first. If a pupil dilating dilution is to be dropped, e.g., into the left eye of a subject, it is presupposed that a pupil area of the left eye before dropping the pupil dilating dilution and a pupil area of the right eye into which the pupil dilating dilution has not been dropped are equal to each other, the left eye having received a drop of the pupil dilating dilution. An index value $k_0$ relating to the increase of the pupil areas of both left and right eyes before dropping the pupil dilating dilution is set to 100%. The pupil area of the left eye $S_0L$ or the pupil area of the right eye $S_0R$ before dropping the pupil dilating dilution is measured and stored. Then, the pupil dilating dilution is dropped into the left eye, and a first measurement is made. The pupil areas of both left and right eyes $S_1L$ and $S_1R$ are measured at this time, and by referring to the pupil areas $S_0L$ and $S_0R$ stored before dropping the pupil dilating dilution, a rate of change in the area of the left eye $S_1L$ (%) and a rate of change in the area of the right eye $S_1R$ (%) are calculated. A difference between these rates of change is further calculated, and an index value $k_1$ relating to the increase of the pupil area of the left eye in the first measurement is calculated from such difference. The calculated index value $k_1$ is then stored. It is this value $k_1$ that faithfully represents the magnification of the pupil of the left eye influenced only by the pupil dilating dilution. Then, a second measurement, a third measurement, and so on to an Nth measurement are similarly made. The aforementioned principle can be expressed in the following equations.

n=0 (before dropping the pupil dilating dilution);
$k_0=100(\%)$
n=1 (after dropping the pupil dilating dilution);
$k_1=S_1L (\%)-S_1R (\%)+100(\%)$
n=N (after dropping the pupil dilating dilution);
$k_N=S_NL (\%)-S_NR (\%)+100(\%)$ When the index value $k_N$ in the Nth measurement exceeds a predetermined value, the subject is diagnosed as having Alzheimer's disease.

Figure 1:
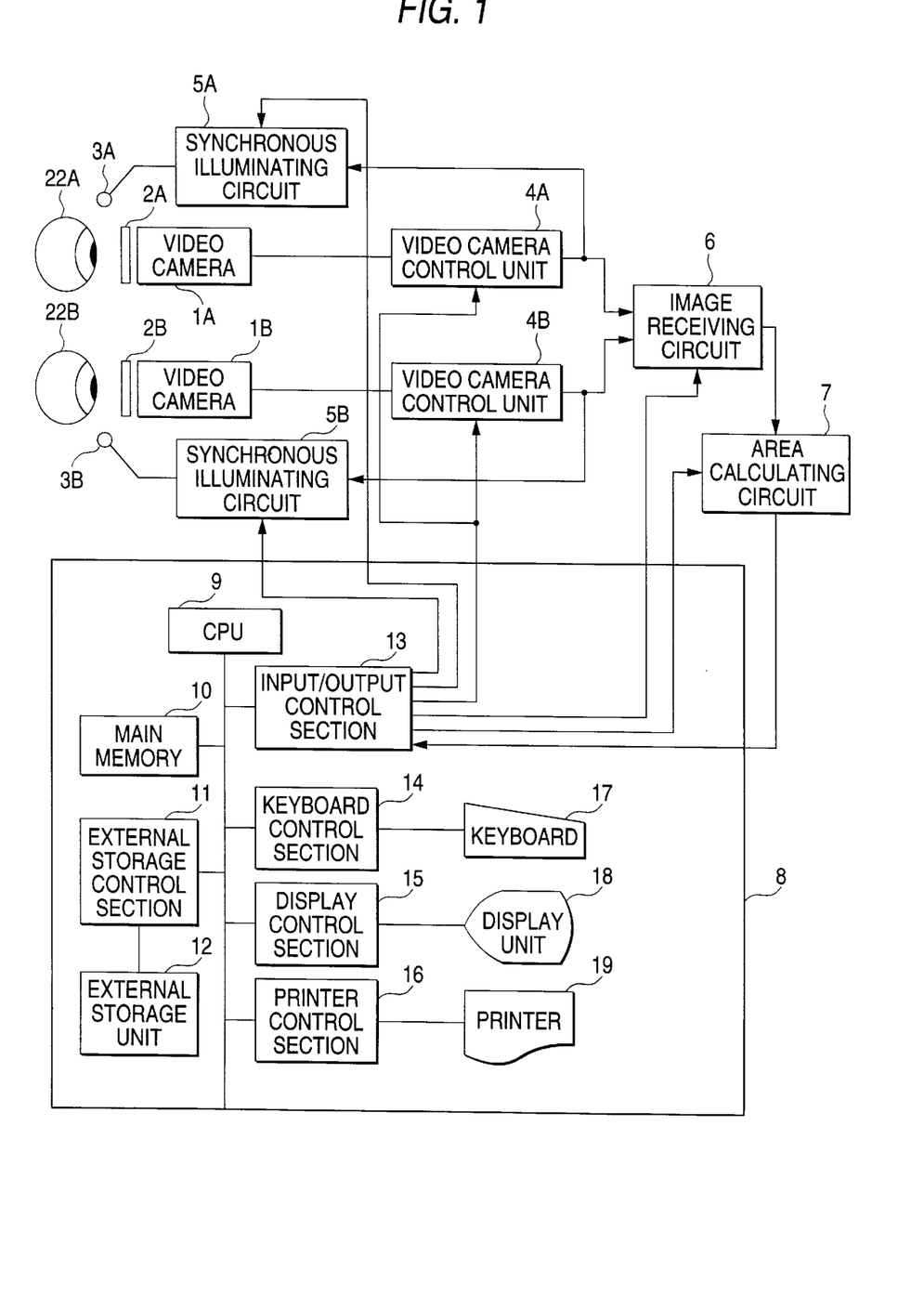
FIG. 1 a diagram showing a general construction of an apparatus, which is a first mode of embodiment.

An apparatus prepared based on the aforementioned principle will be described next. First, a general construction of the apparatus is shown in FIG. 1. As shown in FIG. 1, each of a pair of video cameras 1A, 1B includes an optical lens and an imaging element, and converts an object into a two-dimensional image, divides such image into a plurality of pixels, converts the respective pixels into electric signals, and outputs the electric signals in a predetermined sequence. The imaging elements are constructed of CCDs in this embodiment. In front of the video cameras 1A, 1B are visible light cut filters 2A, 2B. In the proximity to the video cameras 1A, 1B are light sources 3A, 3B. The light sources 3A, 3B are LEDs that emit infrared light.

Figure 2:
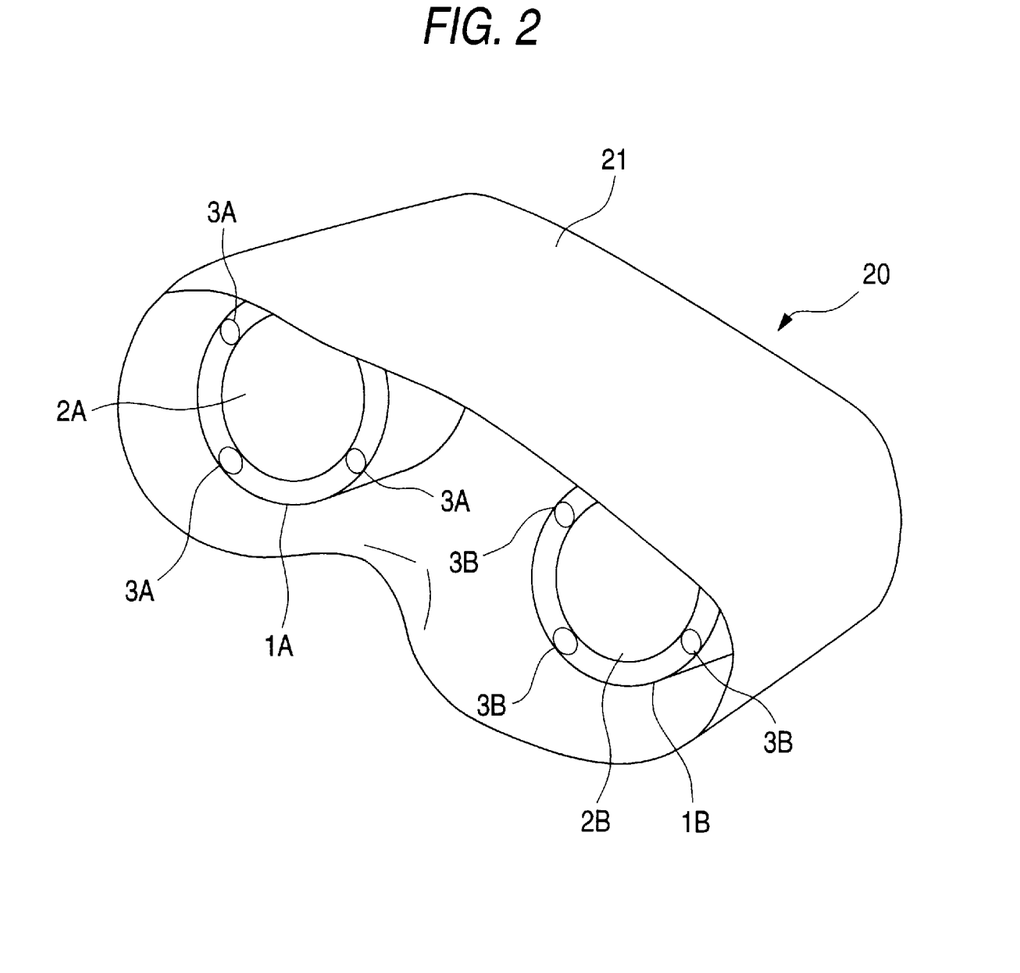
FIG. 2 is a diagram showing the appearance of a goggle.

As shown in FIG. 2, the video cameras 1A, 1B, the visible light cut filters 2A, 2B, the light sources 3A, 3B are the components constituting a goggle 20. That is, these members are attached to a goggle main body 21 and integrated therewith. Each of the light sources 3A, 3B is constructed of a plurality of LEDs, and the plurality of LEDs are disposed circumferentially on the front of the video cameras 1A, 1B. Further, the goggle 20 has a half mirror (not shown), by which a subject can watch an image in the outside.

Returning to FIG. 1, a pair of video camera control units 4A, 4B control not only electronic shutter operation timings of the video cameras 1A, 1B, i.e., exposure cycle and exposure time, but also the outputs of the video cameras 1A, 1B. The video camera control units 4A, 4B also prepare composite video signals into which synchronizing signals are incorporated into video signals, and output such composite video signals. Synchronous illuminating circuits 5A, 5B determine blinking timings of the light sources 3A, 3B based on the synchronizing signals in the composite video signals output from the video camera control units 4A, 4B.

An image receiving circuit 6 receives the outputs of the respective video camera control units 4A, 4B, and stores them temporarily. An area calculating circuit 7 calculates pupil areas of the left and right eyes from data about the images of the left and right pupils received by the image receiving circuit 6.

A digital computer 8 not only controls the video camera control units 4A, 4B, the synchronous illuminating circuits 5A, 5B, the image receiving circuit 6, and the area calculating circuit 7, but also processes output data of the area calculating circuit 7. The digital computer 8 is implemented by a personal computer in this embodiment.

Figure 3:
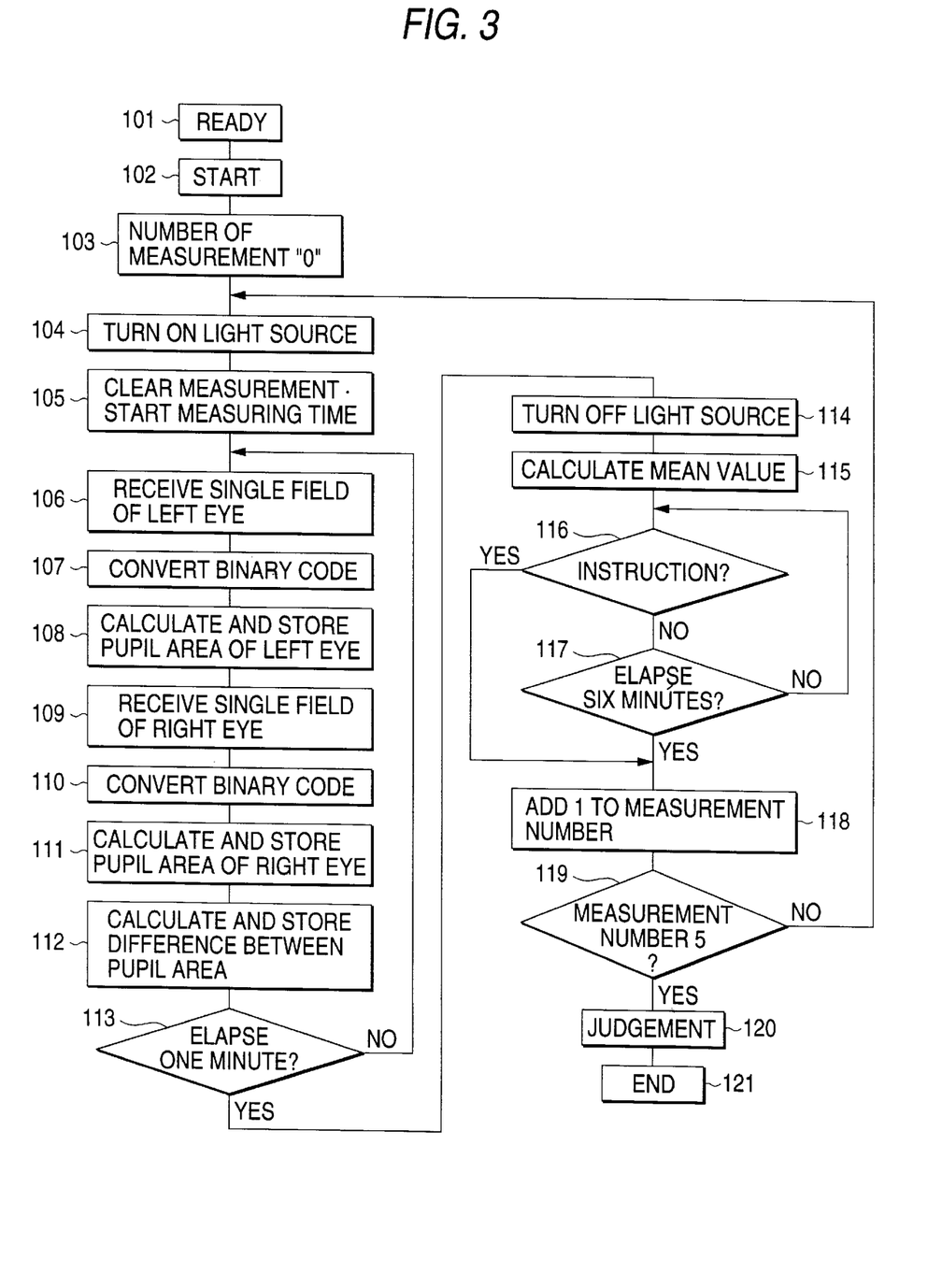
FIG. 3 is a flowchart illustrative of the operation of the apparatus, which is the first mode of embodiment.
Figure 4:
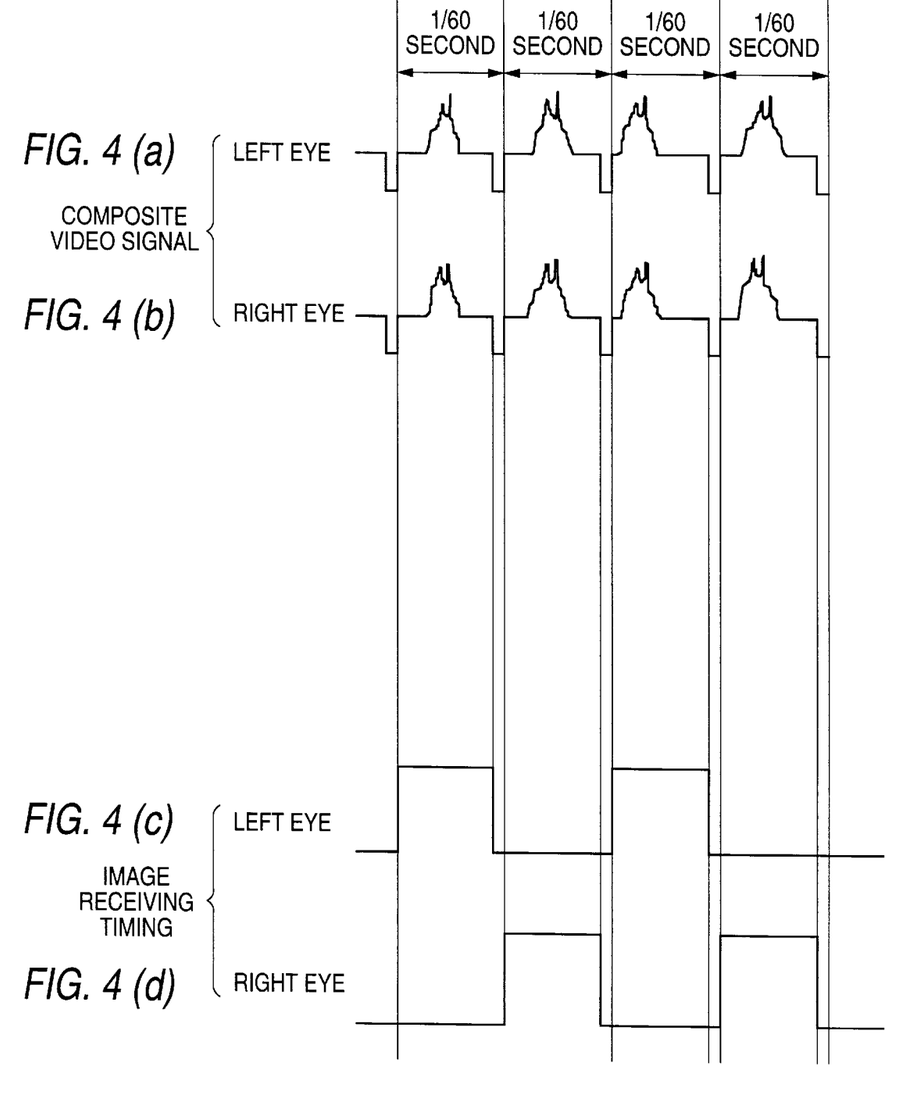

The digital computer 8 includes: a CPU 9; a main memory 10 connected to the CPU 9; an external storage control section 11; an input/output control section 13; a key board control section 14; a display control section 15; a printer control section 16; an external storage unit 12 connected to the external storage control section 11; a key board 17 connected to the key board control section 14; a display 18 connected to the display control section 15; and a printer 19 connected to the printer control section 16. The CPU 9 supervises and controls the overall operation of the digital computer 8, and controls the respective parts and processes data based on programs stored in the main memory 10. The main memory 10 has a ROM (read-only memory) and a RAM (random access memory). The ROM stores programs and data necessary for the CPU 9 to execute a program read to the RAM from the external storage unit 12. The RAM is designed to have the data necessary for the CPU 9 to process and the results obtained by the process written thereto. Various programs and data are stored in the external storage unit 12. A program shown in FIG. 3 is stored in the external storage unit 12 in this embodiment.

The external storage control section 11 controls the reading and writing of data from and to the external storage unit 12 by instructions from the CPU 9. The input/output control section 13 controls reception of data and transmission of control signals from and to external units.

The key board 17 has a plurality of keys. When these keys are pressed, signals corresponding thereto are output. The key board control section 14 controls the output signals of the key board 17 by an instruction of the CPU 9 and stores the controlled output signals in the main memory 10. The display 18 visibly displays given data on a screen thereof. A CRT is used as the display 18 in this embodiment. The display control section 15 displays data stored in the main memory 10 on the display 18 by an instruction of the CPU 9. The printer 19 prints given data on a sheet. A dot printer is used as the printer 19 in this embodiment. The printer control section 16 controls the printer 19 by an instruction of the CPU 9, and causes the printer 19 to print data stored in the main memory 10.

In this embodiment, the video camera device is formed of the video cameras 1A, 1B and the video camera control units 4A, 4B, and the pupil size detecting means is formed of the image receiving circuit 6 and the area calculating circuit 7. In the functions of the digital computer 8, Steps 106 to 115 in FIG. 3 correspond to the reference value detecting means, and Step 120 corresponds to the judging means.

Then, the operation of the thus constructed apparatus according to this embodiment will be described with reference to the flowchart shown in FIG. 3. It is presupposed that the program shown in the flowchart of FIG. 3 is read to the RAM in the main memory 10 from the external storage unit 12 by the operation of the key board 17.

(1) Before dropping a pupil dilating dilution

First, a subject wears the goggle 20 shown in FIG. 2 to get ready for measurement (Step 101). As shown in FIG. 1, the left eye 22A is situated in front of the video camera 1A and the right eye 22B is situated in front of the video camera 1B. Then, the power switch of the apparatus is turned on, so that measurement is started (Step 102). The CPU 9 sets the number of measurements in a measurement number counting area arranged in the RAM of the main memory 10 to 0 (Step 103), and outputs operation start signals to the video camera control units 4A, 4B and the synchronous illuminating circuit 5A, 5B, respectively (Step 104). As a result, composite video signals are output from the video camera control units 4A, 4B, respectively. The synchronous illuminating circuits 5A, 5B synchronize with synchronizing signals outputted from the video camera control units 4A, 4B, and output pulse signals whose cycle is ⅟₆₀ sec and whose width is 1 msec to the light sources 3A, 3B. The light sources 3A, 3B are turned on at the cycle and width specified by such pulse signals. It may be noted that the electronic shutters of the video cameras 1A, 1B are opened by the video camera control units 4A, 4B at the same timing as the timing at which the synchronous illuminating circuits 5A, 5B turn on the light sources 3A, 3B. The image receiving circuit 6 selects and delivers the outputs of the video camera control units 4A, 4B to the area calculating circuit 7 at timings shown in FIG. 4.

Then, in Step 105 shown in FIG. 3, the CPU 9 starts measuring the time and proceeds to Step 106, in which the CPU 9 causes the image receiving circuit 6 to receive a single field of composite video signals of the left eye, converts the received composite video signals into binary codes, and outputs the thus converted data to the area calculating circuit 7 (Step 107). As a result, the area calculating circuit 7 calculates the pupil area of the left eye, and the CPU 9 stores the calculated result (Step 108). Further, the CPU 9 proceeds to Step 109, in which the CPU 9 causes the image receiving circuit 6 to receive a single field of composite video signals of the right eye, converts the received composite video signals into binary codes, and outputs the thus converted data to the area calculating circuit 7 (Step 110). As a result, the area calculating circuit 7 calculates the pupil area of the right eye, and the CPU 9 stores the calculated result (Step 111). Then, the CPU 9 calculates a difference between the pupil area of the left eye and that of the right eye, the pupil areas being calculated by the area calculating circuit 7 (Step 112). That is, the CPU 9 makes the following calculation.

$k=S_nL (\%)-S_nR (\%)$ (n is the number of measurements).

The CPU 9 stores the result in the RAM.

Then, the CPU 9 proceeds to Step 113, in which the CPU 9 judges whether or not one minute has elapsed from the time measurement start. If it is judged that one minute has not yet elapsed, the CPU 9 returns to Step 106, whereas if it is judged that one minute has already elapsed, the CPU 9 proceeds to Step 114, in which the CPU 9 sends signals to turn off the synchronous illuminating circuits 5A, 5B (the light sources are turned off). Then, the CPU 9 proceeds to Step 115, in which the CPU 9 calculates a mean value of the differences between the pupil areas of the left eye and the pupil areas of the right eye so far obtained, and stores the calculated mean value in the RAM of the main memory 10 so as to be tied with the corresponding number of measurements.

Then, the CPU 9 proceeds to Step 116, in which the CPU 9 judges whether or not a measurement start instruction has been given through the operation of the key board 17. If it is judged that such instruction has been given, the CPU 9 proceeds to Step 118 and adds 1 to the content of the measurement number counting area. If, on the other hand, it is judged in Step 116 that no such instruction has been given, the CPU 9 proceeds to Step 117, in which the CPU 9 judges whether or not six minutes have elapsed from the time measurement start in Step 105. If it is judged affirmatively, the CPU 9 proceeds to Step 118, whereas if it is judged negatively, the CPU 9 returns to Step 116.

Here, before six minutes elapse, the examiner removes the goggle 20 from the subject, and drops the pupil delating dilution into the left eye and a physiological saline into the right eye. Then, the subject wears the goggle 20 again. After having checked that the subject has worn the goggle 20 correctly, the examiner enters a measurement start instruction by operating the key board 17.

(2) After the pupil dilating dilution has dropped

Figure 5:
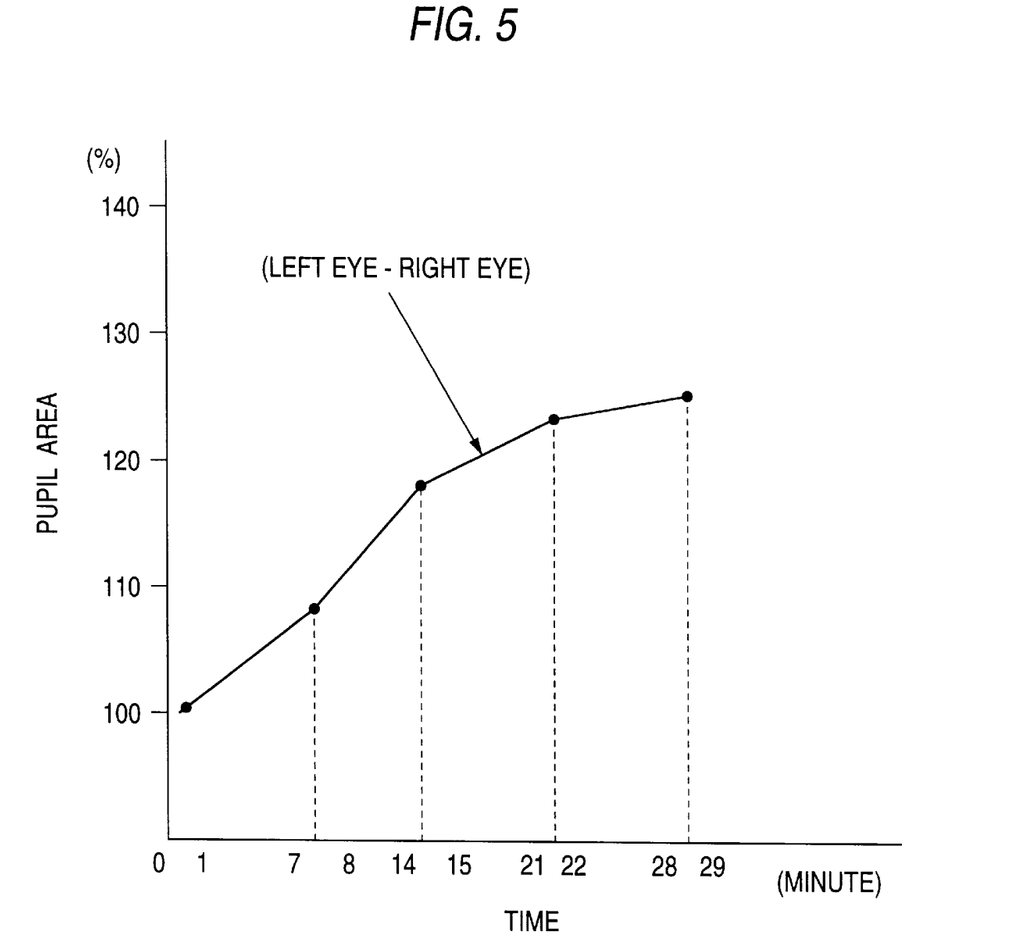
FIG. 5 is a diagram illustrative of measured results obtained by the apparatus, which is the first mode of embodiment.

When the measurement start instruction has been entered in Step 116 shown in FIG. 3, the CPU 9 proceeds to Step 118, in which the CPU 9 adds 1 to the content of the measurement number counting area. Then, the CPU 9 proceeds to Step 119, in which the CPU 9 judges whether or not the content of the measurement number counting area is 5. If it is judged negatively, the CPU 9 returns to Step 104, whereas if it is judged affirmatively, the CPU 9 proceeds to Step 120, in which the CPU 9 judges whether or not the subject has contracted Alzheimer's disease. That is, the processing from Steps 104 to 119 is repeated until five measurements are counted, and the magnification of the pupil area such as shown in FIG. 5 is displayed in the form of a graph. The judgment in Step 120 is made as follows.

The CPU 9 judges that the subject suffers from Alzheimer's disease when the value obtained in the last one-minute measurement (the fifth measurement) exceeds 134%, judges that the subject does not suffer from Alzheimer's disease if the value does not exceed 134%, and displays the result of the judgment on the display 18.

Figure 6:
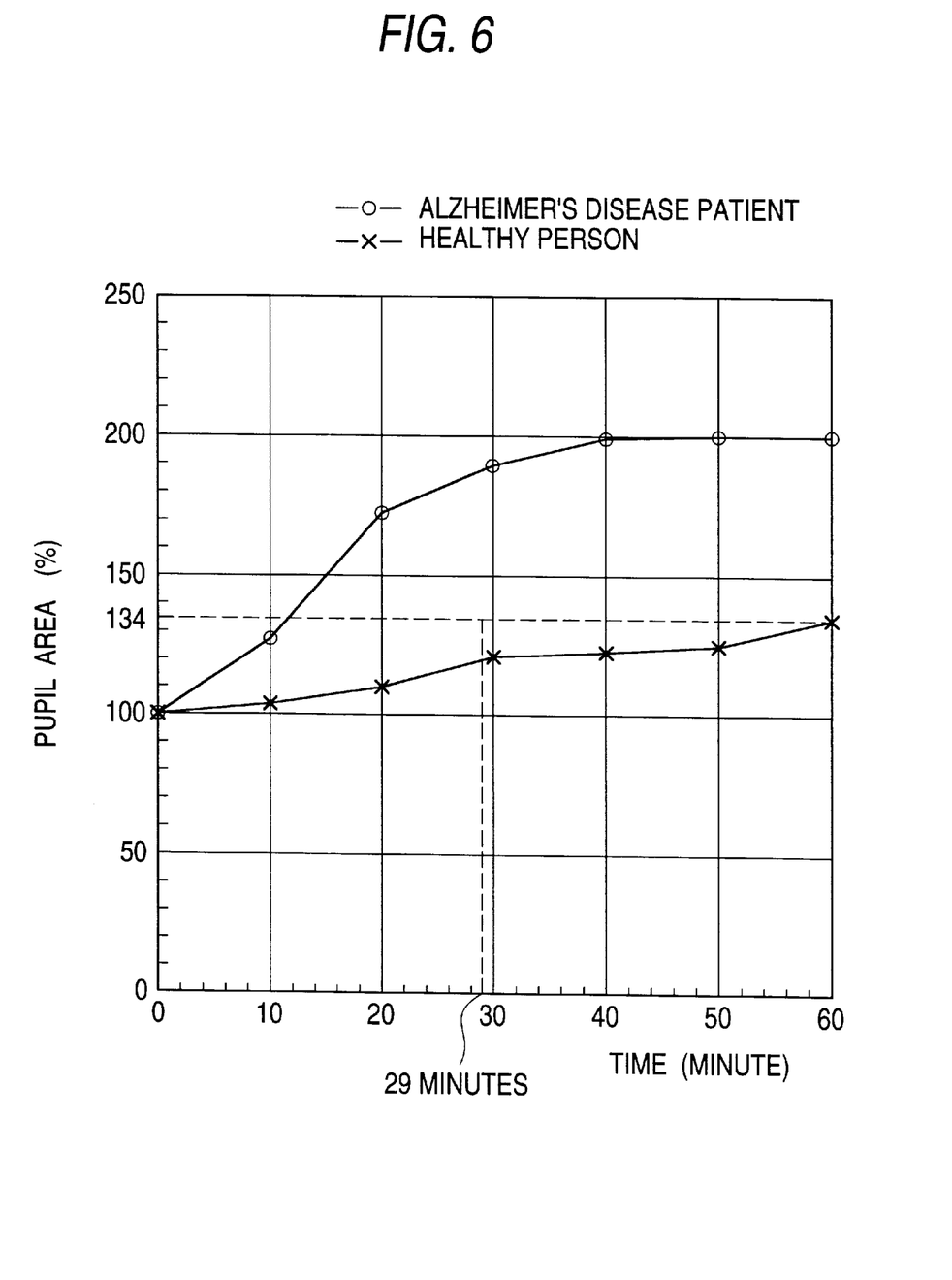
FIG. 6 is a diagram showing the magnification of the pupil area of a patient suffering from Alzheimer's disease and that of a healthy person.

The reason why such judgment is made will be described next. First, when the one-minute measurement has been made for 5 times, data such as shown in FIG. 5 are displayed on the screen of the display 18. Here, the magnification of the pupil area of a patient affected with Alzheimer's disease is obviously different from that of a subject not affected with Alzheimer's disease as shown in FIG. 6, the magnification being obtained at the time the last one-minute measurement has been completed. The magnification of the pupil area of the patient affected with Alzheimer's disease is 134% or more.

Figure 7:
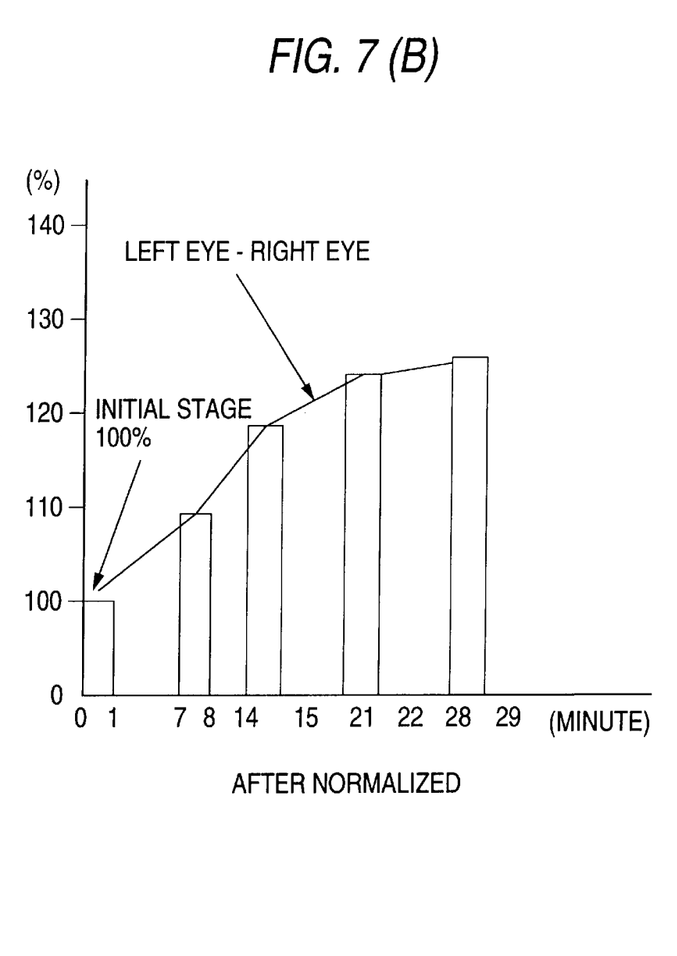
FIG. 7A and FIG. 7(B) are diagrams showing a specific example of a pupil area measurement using the apparatus, which is the first mode of embodiment.
Figure 8:
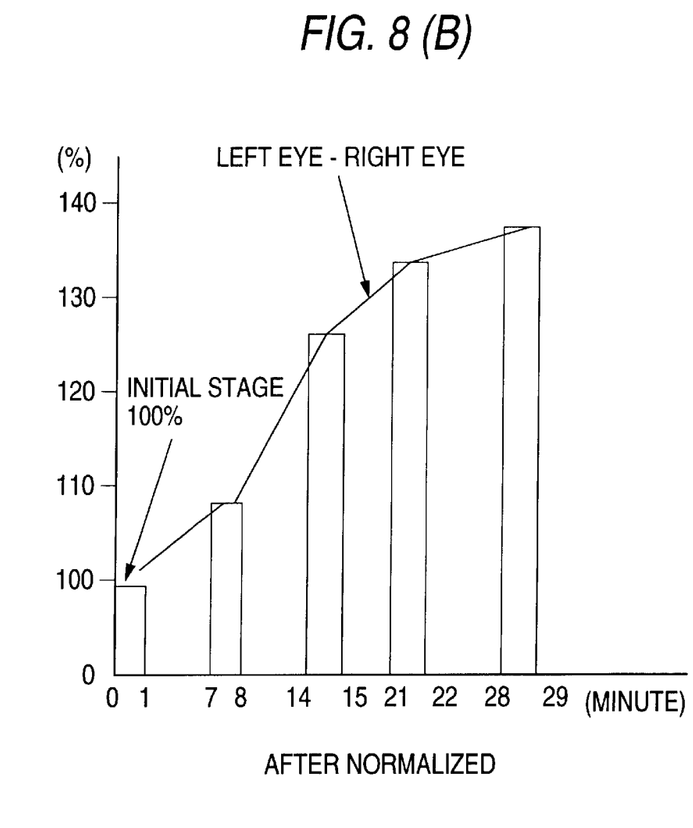
FIG. 8(A) and FIG. 8(B) are diagrams showing a specific example of a pupil area measurement using the apparatus, which is the first mode of embodiment.
Figure 9:
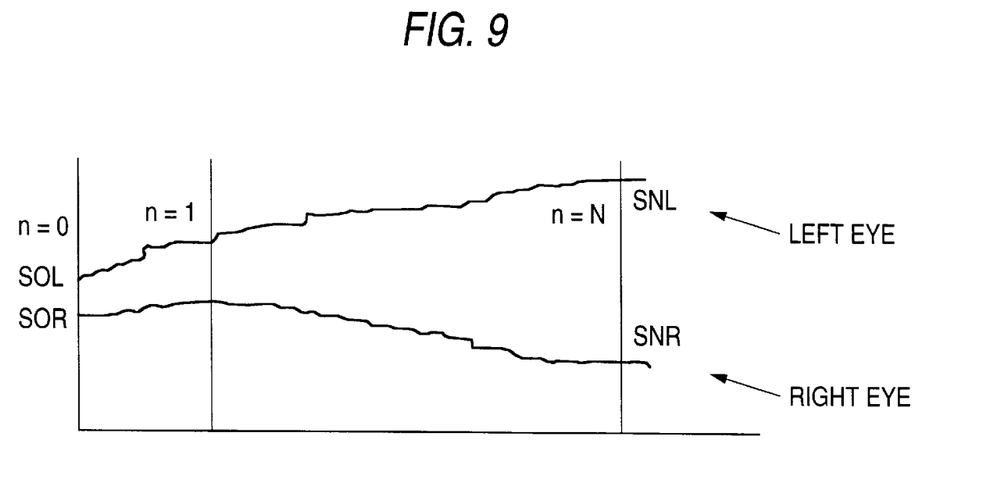
FIG. 9 is a diagram illustrative of the principle of a second mode of embodiment.

Two specific examples taken using the apparatus according to this embodiment are shown in FIGS. 7 and 8. FIG. 7 shows an example in which a room becomes darker as the measuring time elapses. FIG. 7 (A) shows changes in the pupil area of the left eye and the right eye. It is considered that the pupil area of the left eye dilates because the pupil dilating dilution has been dropped into the left eye. The pupil area of the right eye into which the pupil dilating dilution has not been dropped also dilates. This increase of the pupil area of the right eye accounts for the fact that the pupil area increases in response to the degree of darkness in the room. This factor, i.e., the response to the degree of darkness in a room, has also given an influence upon the increase of the pupil area of the left eye into which the pupil dilating dilution has been dropped. That is, it is considered that the pupil area of the left eye is further increased by the fact that the room is dark.

FIG. 7 (B) is a normalized graph from which influences derived from changes in the lightness of a room are removed. Thus, by referring to a difference between a pupil area of the left eye and a pupil area of the right eye, the magnification of a pupil influenced only by the fact that the pupil dilating dilution has been dropped can be correctly calculated free from the influences derived from changes in the lightness of the room.

FIG. 8 shows an example in which a pupil is influenced by autonomic unbalance or pupil compensation action. FIG. 8 (A) shows changes in the pupil area when pupils have received such influence. This is a case where it is considered that a patient felt too bright because the pupil of the left eye into which the pupil dilating dilution has been dropped dilated, so that the pupil of the right eye contracted conversely by natural pupil compensation action.

FIG. 8 (B) is a normalized graph obtained from differences between pupil areas of the left eye and pupil areas of the right eye in order to remove such influences. As a result, the magnification of the pupil influenced only by the fact that the pupil dilating dilution has been dropped can be obtained correctly.

A second embodiment of the invention will be described. The principle of this embodiment will be described first. In this cases measurement can be made even if a pupil area of the left eye into which the pupil dilating dilution is to be dropped is different from a pupil area of the right eye into which the pupil dilating dilution is not to be dropped before dropping the pupil dilating dilution.

A pupil area of the left eye SOL and a pupil area of the right eye $S_0R$ before dropping the pupil dilating dilution are measured and stored. Then, the pupil dilating dilution is dropped into the left eye to make a first measurement. During the measurement, a pupil area of the left eye $S_1L$ and a pupil area of the right eye $S_1R$ are measured, and a difference D between a difference D1 and a difference DO is calculated, the difference D1 being between the pupil area of the left eye $S_1L$ and the pupil area of the right eye $S_1R$ and the difference D0 being between the pupil area of the left eye $S_0L$ and the pupil area of the right eye $S_0R$ before dropping the pupil dilating dilution. This difference D is stored as an index value $k_1$ relating to the magnification of the pupil area of the left eye in the first measurement. A second measurement, a third measurement, and so on to an Nth measurement are similarly made thereafter. These measurements can be expressed by the following equations.

n=1 (after dropping the pupil dilating dilution)
$k_1 = \{S_1L \ (mm^2) - S_1R \ (mm^2)\} - \{S_0L \ (mm^2) - S_0R \ (mm^2)\}$ n=N (after dropping the pupil dilating dilution)
$k_N = \{S_NL \ (mm^2) - S_NR \ (mm^2)\} - \{S_0L \ (mm^2) - S_0R \ (mm^2)\}$ If the measured value $k_N$ obtained in the Nth measurement exceeds a predetermined value, then the subject is diagnosed as having Alzheimer's disease.

An apparatus that is prepared based on the aforementioned principle will be described next. Although the hardware configuration of this apparatus is the same as that of the apparatus shown in FIG. 1, this apparatus is distinguished from the apparatus shown in FIG. 1 in that the CPU 9 makes a calculation with the following equation in Step 112 shown in FIG. 5 among the processing steps executed by the CPU 9.

$k_n = \{S_nL \ (mm^2) - S_0R \ (mm^2)\} - \{S_0L \ (mm^2) - S_0R \ (mm^22)\}$

Further, the judgment made in Step 120 is based on 4.27 mm². The second mode of embodiment provides functions and advantages similar to those of the first mode of embodiment.

While the pupil area is used as the size of a pupil in the aforementioned modes of embodiment, the pupil diameter may be used to provide similar functions and advantages as long as the pupil diameter is similarly processed.

While the aforementioned description refers to the judgment on whether or not a subject has contracted Alzheimer's disease, a judgment on whether or not a subject has contracted autonomic unbalance can be similarly made as long as the eyedrops, measurement time, and criteria are changed.

According to the invention, an index value relating to the magnification of a pupil which is faithfully influenced only by an eyedrops can be obtained. Therefore, whether or not a subject suffers from a specific disease can be judged correctly.

What is claimed is:

1. A disease judging apparatus, comprising:

a video camera device for respectively imaging pupils of a left eye and a right eye of a subject with one of the left eye and the right eye having eyedrops applied thereto;

pupil size detecting means for calculating a size of the pupil of the left eye and a size of the pupil of the right eye a plurality of times by processing video output signals from the video camera device;

index value detecting means for calculating an index value relating to a change in the size of the pupil into which the eyedrops have been applied from the change in size of the pupil of the other eye detected by the pupil size detecting means at each of the plurality of times; and judging means for judging whether the subject suffers from the disease by comparing the index value with a predetermined value.

2. A disease judging apparatus according to claim 1, wherein the index value detecting means calculates the index value based on a difference between a rate of change in the size of the pupil of the left eye and a rate of change in the size of the pupil of the right eye.

3. A disease judging apparatus according to claim 1, wherein the index value detecting means calculates the index value based on a rate of change in a difference between the size of the pupil of the left eye and the size of the pupil of the right eye.

4. A disease judging method, comprising:

imaging pupils of a left eye and a right eye of a subject wherein one of the left eye and the right eye have eyedrops applied thereto to generate video output signals;

calculating a size of the pupil of the left eye and a size of the pupil of the right eye at a plurality of times processing the video output signals;

calculating an index value relating to a change in the size of the pupil into which the eyedrops have been applied from the size of the pupil of the other eye detected at each of the plurality of times; and judging whether the subject suffers from the disease by comparing the index value with a predetermined value.

5. A disease judging method as claimed in claim 4, wherein the index value is calculated based on a difference between a rate of change in the size of the pupil of the left eye and a rate of change in the size of the pupil of the right eye.

6. A disease judging method according to claim 4, wherein the index value is calculated based on a rate of change in a difference between the size of the pupil of the left eye and the size of the pupil of the right eye.

7. A disease judging apparatus, comprising:

a video camera which images pupils of a left eye and a right eye of a subject with one of the left eye and the right eye having eyedrops applied thereto;

a calculator which calculates a size of the pupil of the left eye and a size of the pupil of the right eye a plurality of times by processing video output signals from the video camera device;

an index calculator which calculates an index value relating to a change in the size of the pupil into which the eyedrops have been applied from the size of the pupil of the other eye detected at by the area calculator at each of the plurality of times; and a comparator which compares the index value with a predetermined value to determine whether the subject suffers from the disease.

8. Disease judging apparatus, comprising:

a video camera device for respectively imaging pupils of a left eye and a right eye of a subject with one of the left eye and the right eye having eyedrops applied thereto;

first means for calculating a size of the pupil of the left eye and a size of the pupil of the right eye a plurality of times by processing video output signals from the video camera device;

second means for calculating an index value relating to a change in the size of the pupil into which the eyedrops have been applied from the change in size of the pupil of the other eye detected by the first means at each of the plurality of times; and third means for judging whether the subject suffers from the disease by comparing the index value with a predetermined value.

* * * * *